(12) United States Patent
Asim et al.

(10) Patent No.: US 9,031,231 B2
(45) Date of Patent: May 12, 2015

(54) DEVICE AND USER AUTHENTICATION

(75) Inventors: Muhammad Asim, Eindhoven (NL);
Jorge Guajardo Merchan, Eindhoven (NL); Milan Petkovic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 668 days.

(21) Appl. No.: 13/263,854

(22) PCT Filed: Apr. 2, 2010

(86) PCT No.: PCT/IB2010/051448
§ 371 (c)(1),
(2), (4) Date: Oct. 11, 2011

(87) PCT Pub. No.: WO2010/116310
PCT Pub. Date: Oct. 14, 2010

(65) Prior Publication Data
US 2012/0033807 A1  Feb. 9, 2012

(30) Foreign Application Priority Data
Apr. 10, 2009  (EP) ..................................... 09157811

(51) Int. Cl.
*H04L 9/00* (2006.01)
*H04L 9/08* (2006.01)
*G06F 19/00* (2011.01)
(Continued)

(52) U.S. Cl.
CPC ............. *H04L 9/0866* (2013.01); *G06F 19/323* (2013.01); *G06F 21/32* (2013.01); *G06F 21/34* (2013.01); *G06F 2221/2129* (2013.01); *H04L 9/3231* (2013.01); *H04L 2209/88* (2013.01)

(58) Field of Classification Search
CPC ...... H04L 9/0866; H04L 9/3231; G06F 21/32

USPC .......................................................... 380/44
See application file for complete search history.

(56) References Cited

U.S. PATENT DOCUMENTS 6,154,879 A  11/2000  Pare, Jr. et al.
6,564,056 B1  5/2003  Fitzgerald
(Continued)

FOREIGN PATENT DOCUMENTS

EP  1791073 A1  5/2007
JP  2002541533 A  12/2002
(Continued)

OTHER PUBLICATIONS

Golic et al. Entropy Analysis and New Constructions of Biometric Key Generation Systems, 2008, Retrieved from the Internet <URL: ieeexplore.ieee.org/xpls/abs_all.jsp?arnumber=4494684&tag=1>, pp. 1-15 as printed.*

Linnartz et al., New Shielding Functions to Enhance Privacy and PRevent Misuse of Biometric Templates, 2003, Retrieved from the Internet <URL: link.springer.com/chapter/10.1007%2F3-540-44887-X_47>, pp. 1-10 as printed.*

(Continued)

*Primary Examiner* — Michael Chao

(57) ABSTRACT

A method of authenticating a device and a user comprises obtaining a device ID for the device, performing a biometric measurement of the user, obtaining helper data for the user, and generating a key from the biometric measurement and helper data. There is then generated a message comprising the key or a component derived from the key, which transmitted to a remote service, and at the service there is carried out the step of authenticating the device and the user with the message. In a preferred embodiment, the generating of the key further comprises generating the key from the device ID.

20 Claims, 10 Drawing Sheets

(51) Int. Cl.
  *G06F 21/32*   (2013.01)
  *G06F 21/34*   (2013.01)
  *H04L 9/32*    (2006.01)

(56) References Cited

U.S. PATENT DOCUMENTS

| | | | |
|---|---|---|---|
| 2001/0052077 A1* | 12/2001 | Fung et al. | 713/184 |
| 2003/0023882 A1* | 1/2003 | Udom | 713/202 |
| 2005/0204134 A1 | 9/2005 | Arx et al. | |
| 2005/0286746 A1* | 12/2005 | Silvester | 382/116 |
| 2006/0246921 A1 | 11/2006 | Russ | |
| 2007/0014407 A1 | 1/2007 | Narendra et al. | |
| 2008/0282343 A1 | 11/2008 | Schrijen et al. | |
| 2009/0183248 A1 | 7/2009 | Tuyls et al. | |
| 2010/0027784 A1 | 2/2010 | Tuyls et al. | |
| 2011/0191837 A1 | 8/2011 | Merchan et al. | |

FOREIGN PATENT DOCUMENTS

| | | | |
|---|---|---|---|
| JP | 2008516472 A | 5/2008 | |
| JP | 2008526080 A | 7/2008 | |
| WO | 2005066871 A2 | 7/2005 | |
| WO | 2006067739 A2 | 6/2006 | |

OTHER PUBLICATIONS

Jo et al.; Biometric Digital Signature Key Generation and Cryptography Communication Based on Fingerprint; 2007; Retrieved from the Internet <URL: http://link.springer.com/chapter/10.1007/978-3-540-73814-5_4>; pp. 1-12 as printed.*

No stated author; Recommendations for Proper User Identification in Continua v. 1—PAN and xHR Interfaces; Continua health alliance; 2007; Retrieved from the Internet <URL: cw.continuaalliance.org/document/dl/download/3734>; pp. 1-27 as printed.*

Linnartz et al, "New Shielding Functions to Enhance Privacy and Prevent Misuse of Biometric Templates", Audio and Video Based Biometric Person Authentication, AVBPA, Ser. LNCS, 2003 pp. 1-9.

Dodis et al, "Fuzzy Extractors: How to Generate Strong Keys From Biometrics and Other Noisy Data", Advances in Cryptology, Eurocrypt, Ser. LNCS, 2004, pp. 1-18.

Carter et al, "Universal Classes of Hash Functions", Jounral of Computer and System Science, vol. 18, 1979, pp. 143-154.

Salt (Cryptography) From Wikipedia, The Free Encyclopedia, Downloaded From http://en.wikipedia.org/wiki/password_salt, 2008, 3 page Document.

* cited by examiner

DEVICE AND USER AUTHENTICATION

TECHNICAL FIELD OF THE INVENTION

This invention relates to a method of, and system for, authenticating a device and a user. The invention can be used to provide enhanced patient authentication for health services with using device ID.

BACKGROUND TO THE INVENTION

An increasingly important trend in healthcare is one of consumer/patient involvement at all levels of healthcare. People are taking a more active role in their own health management. This trend of patient empowerment has already been widely supported. A number of solutions have been introduced in the market that allow patients to collect their own health-related information and to store them on portable devices, PCs, and in online services (e.g. CapMed, WebMD, MedKey). These solutions are often referred to as Personal Health Record (PHR) services. Already a number of products in the market allow patients to automatically enter measurements and other medical data into their PHR (for example LifeSensor and Microsoft HealthVault). In such a system a weight-scale, for example, will send its information via Bluetooth to a PC from which the data is then uploaded to the user's PHR. This allows patients to collect and manage their own health data, but even more importantly, to share the data with various healthcare professionals involved in their treatment.

Another important trend in healthcare is that the delivery of healthcare has been gradually extended from acute institutional care to outpatient care and home care. Advances in information and communication technologies have enabled remote healthcare services (telehealth) including telemedicine and remote patient monitoring to be developed. A number of services in the market already deploy telehealth infrastructures where the measurement devices are connected via home hubs to remote backend servers. Health care providers use this architecture to remotely access the measurement data and help the patients. Examples are disease management services (such as Philips Motiva and PTS) or emergency response services (Philips Lifeline).

Interoperability of measurement devices, home hubs and backend services becomes very important for enabling and further growth of this market. This need is recognized by the Continua health alliance. As shown in FIG. 1, this initiative standardizes protocols between measurement devices, home hub (application hosting) devices, online healthcare/wellness services (WAN) and health record devices (PHRs/EHRs). Next to data format and exchange issues, Continua is also addressing security and safety issues.

One of the basic security problems in the domain of telehealth is the problem of user and device authentication/identification. Namely, when data remotely measured by patients is used by telehealth services or in the medical professional world, the healthcare providers need to place greater trust in information that patients report. In particular, the service providers have to be satisfied that a measurement is coming from the right patient, and that appropriate device was used to take the measurement. Considering, for example, a blood pressure measurement, it is crucial to know that the blood pressure of a registered user is measured (not of his friends or children), and that the measurement was taken by a certified device and not a cheap fake device. This is very important, because there can be critical health care decisions made based on wrong data. So, user authenticity and device authenticity must be supported. This has the benefits of patient safety (diagnosis and health decisions are based on reliable data with established data provenance), reduction of costs (reuse of patient provided data in the consumer health and the professional healthcare domain is supported as data is reliable) an convenience for the patient (they can take healthcare measurements at home)

In current practice, a device identifier (device ID) is either used as a user identifier (user ID) or as a means to derive a user ID (if multiple users are using the same device). For example, in Continua, as described in Continua Health Alliance, "Recommendations for Proper User Identification in Continua Version 1—PAN and xHR interfaces" (Draft v.01) December 2007, at the PAN interface (see FIG. 1), each Continua device is required to send its own unique device ID. The user ID is optional (and can be just simple as 1, 2, A, B). The valid user ID is obtained at the hub device (application hosting device) which can provide mapping between a simple user ID associated with a device ID to a valid user ID. There might be also measurement devices that can send a valid user ID next to the device ID. Then the mapping is not needed.

There are several problems with this current approach. Firstly, the current approach does not support authentication of users/devices, it only appends the user ID to the measurement. Data origin is not established, as a healthcare provider later in the process cannot securely find which device was used to create the measurement. Secondly, the current mapping approach does not quickly associate the user and device ID, but it introduces room for mistakes. Either a user makes an unintended mistake (if manual mapping is required—the user has to select his ID at application hosting device or measurement device for each measurement) or system can mix the users (the application designer should take special care to provide data management in a way to reduce the potential for associating measurements to the wrong user). Thirdly, a malicious user can introduce wrong measurements by impersonating the real user.

SUMMARY OF THE INVENTION

It is therefore an object of the invention to improve upon the known art.

According to a first aspect of the present invention, there is provided a method of authenticating a device and a user comprising obtaining a device ID for the device, performing a biometric measurement of the user, obtaining helper data for the user, generating a key from the biometric measurement and helper data, generating a message comprising the key or a component derived from the key, transmitting the message to a remote service, and authenticating the device and the user with the message.

According to a second aspect of the present invention, there is provided a system for authenticating a device and a user comprising a measurement apparatus arranged to perform a biometric measurement of the user, and a processor arranged to obtain a device ID for the device, obtain helper data for the user, generate a key from the biometric measurement and helper data, generate a message comprising the key or a component derived from the key, and transmit the message to a remote service.

Owing to the invention, it is possible to provide a method to bind the identity of a user and a device identifier so as to certify that data originating from the device originates from the specific device and the specific user. Different embodiments are provided for closely binding the identity of the patient to the device ID, with the assumption that each health care device has a unique ID which is not modifiable. This supports data quality assurance and reliability in personal healthcare applications. To ensure proper device and user authentication/identification the use of Global Unique ID of each device in combination with biometrics is used. The invention provides close coupling of the user ID and the identifier of the device used to take the measurement in which the use of unregistered device/user is immediately detected and strong user authentication using biometrics.

In a preferred embodiment, the step of generating a key further comprises generating the key from the device ID. One way in which the user's biometric information and the device ID can be tightly bound together at an early stage in the process is for the device ID to be used in the generation of the key that will be used in the secure process. The biometric information plus the helper data and the device ID are used to generate the key, which may then be sent with the sensing data obtained from the device.

Advantageously, the method further comprises obtaining sensing data for the user, and the component derived from the key comprises the sensing data processed with the key. The key can be used to sign the sensing data that is included in the message sent to the service provider. This provides a simple and efficient method of using the generated key to secure the sensing data and also ensures that the authentication process will identify the device and user that provided the sensing data.

In a further embodiment, the method comprises generating a codeword from the biometric measurement and helper data, and checking that the device ID matches the codeword. This supports a process by which the device ID can be checked prior to the sending of the message to the third party service provider. An alert can be issued to the user at this time, but it is still that the case that a secure method of authenticating the user and the device that they are currently using is provided.

In a yet further embodiment, the step of generating a message further comprises including the helper data for the user in the message and the step of authenticating the device and the user comprises generating the key from the helper data and the device ID. This methodology enables a secure transmission of the information about the device and user because the authentication at the service side generates the key required from the helper data and the device ID. If either of the user of device are wrong, then the correct key cannot generated.

In a yet further embodiment, the process further comprises encrypting the device ID with the key and wherein the component derived from the key comprises the encrypted device ID. Rather than generating the key with the device ID and the transmitting the key in the message, the system can encrypt the device ID with the key generated from the biometric data and the user's helper data. This will still ensure that the user and device can be authenticated at the service end, in a secure manner.

BRIEF DESCRIPTION OF THE DRAWINGS

Embodiments of the present invention will now be described, by way of example only, with reference to the accompanying drawings, in which:—

DETAILED DESCRIPTION OF THE PREFERRED EMBODIMENTS

Figure 1:
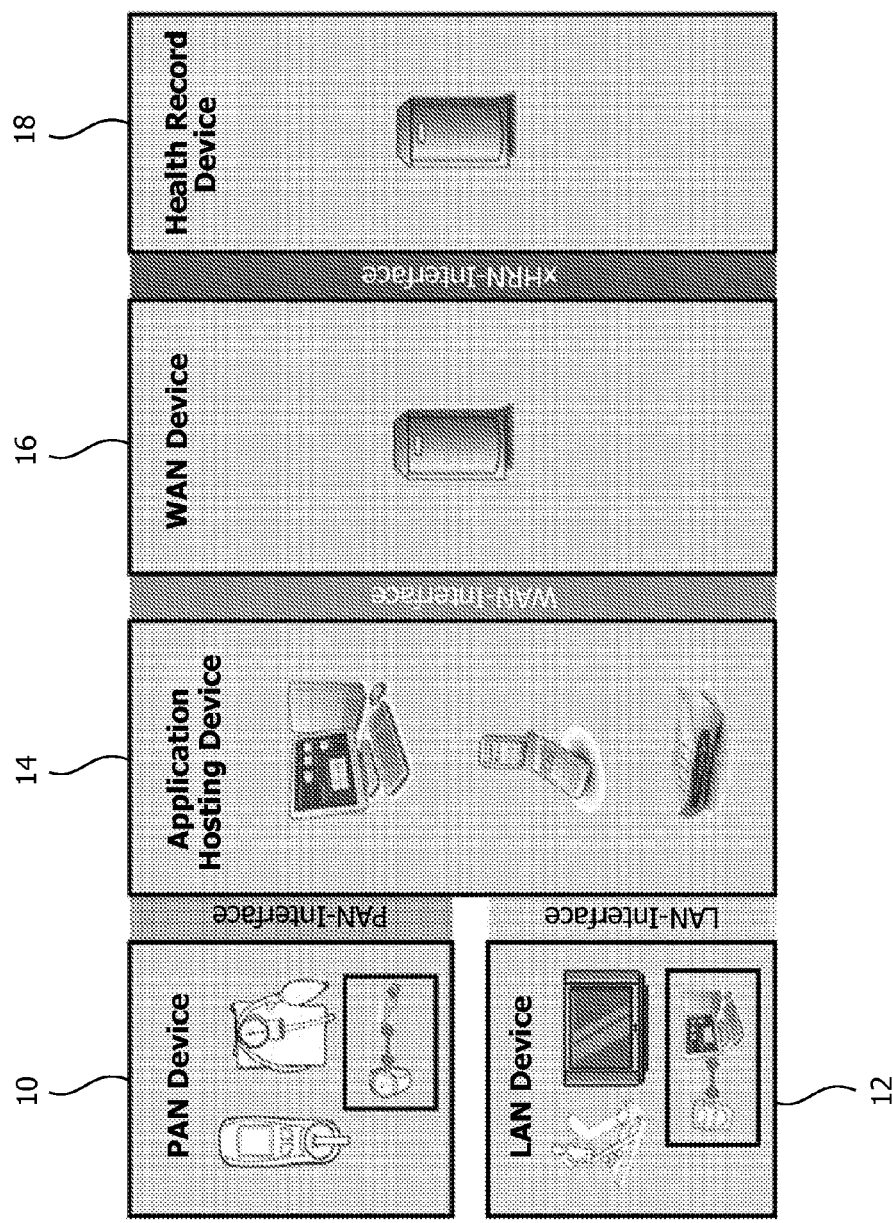
FIG. 1 is a schematic diagram of a healthcare system.

An example of a healthcare system is shown in FIG. 1. Various PAN (personal area network) devices 10 are shown such as a wristwatch and a blood pressure measuring device, which directly measure physiological parameters of a user. Additionally LAN (local area network) devices 12 are provided such as a treadmill which can also be used to gather further healthcare information about the user. The PAN devices 10 and the LAN devices 12 are connected via suitable interfaces (wired and/or wireless) to an appropriate application hosting device 14, such a computer or mobile phone, which will be local to the PAN and LAN devices 10 and 12, for example, in the home of the user. The hosting device 14 will be running a suitable application which can gather and organize the outputs from the various PAN and LAN devices 10 and 12.

The application hosting device 14 is connected to a WAN (wide area network) device 16 such as a server. The WAN connection can be via a network such as the Internet. The server 16 is also connected via a suitable interface to a health record device 18, which is maintaining a health record for the users of the system. Each user has a health record stored in the device 18. As discussed above, it is of paramount importance that the data recorded by the individual health records stored by the device 18 is assigned, firstly to the correct user, and additionally, that the device 10 or 12 which originally recorded the data is known with absolute certainty. It is also advisable that the relevant PAN or LAN device 10 or 12 is also approved for use in the system.

Figure 2:
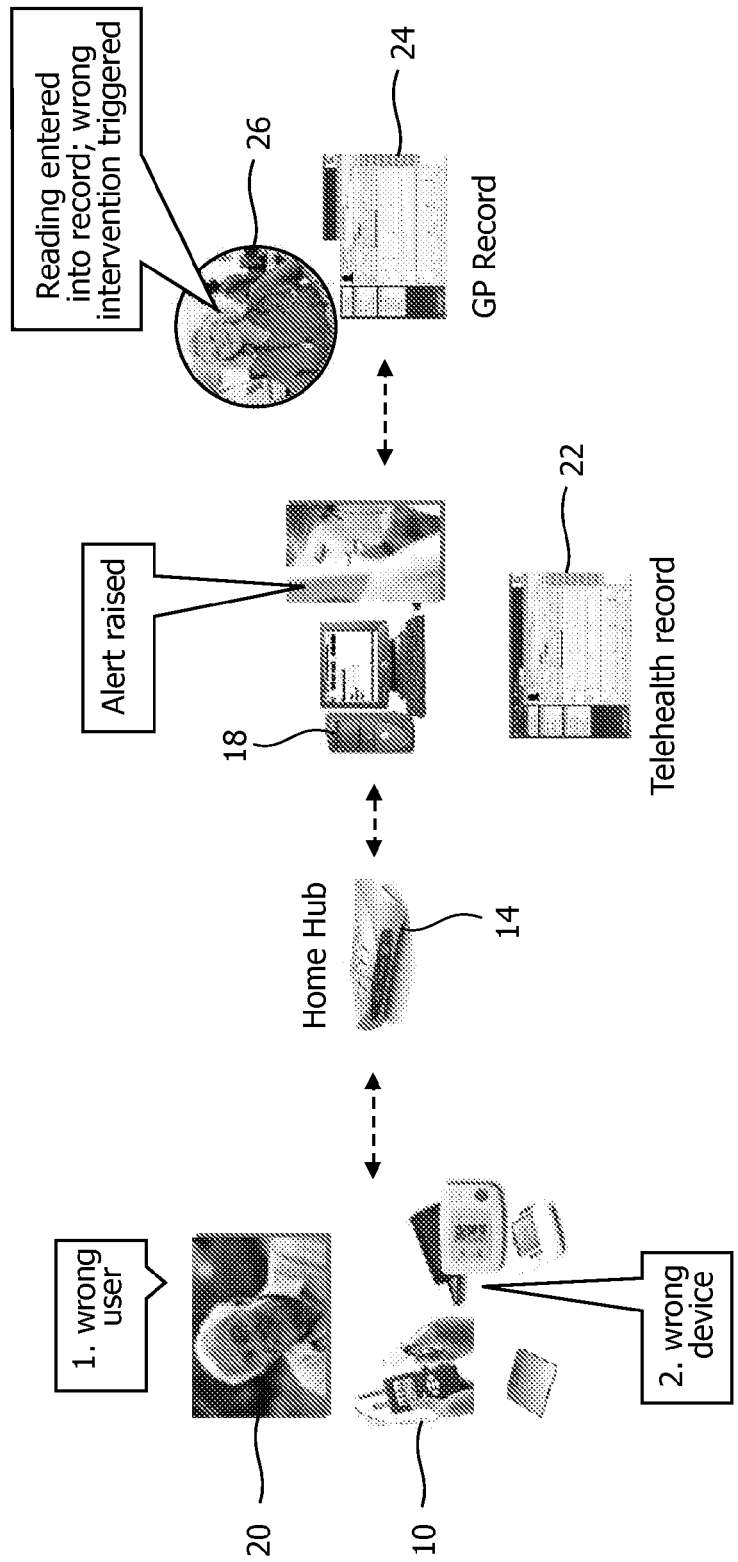
FIG. 2 is a further schematic diagram of the healthcare system.

FIG. 2 illustrates the system of FIG. 1, with a user 20 who is taking a measurement with a PAN device 10. Through the home hub 14, data can be communicated to the remote record device 18, which is maintaining the patient's record 22. The remote record device 18 also communicates directly with a GP record 24. In this example, the user 20 has wrongly identified themselves to the device 10, and is also using an incorrect device 10, for the measurement that they are trying to make. In a conventional system, this will result in an incorrect entry being made in their record 22, and could cause an incorrect alert to be raised with respect to the patient's condition.

Figure 3:
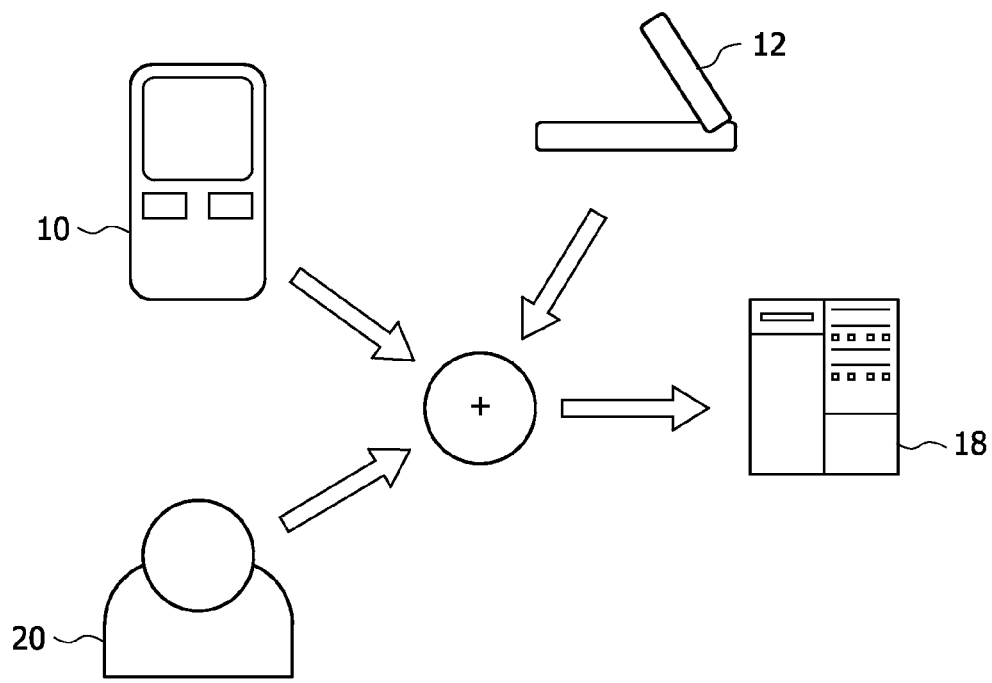
FIG. 3 is a schematic diagram of a device and user authentication system.

In order to prevent the kind of error that is illustrated by FIG. 2, the system according to the present invention is summarized in FIG. 3. This Figure shows a PAN device 10, a LAN device 12 and the user 20, communicating with the remote healthcare device 18. The essential principle is that a key is derived from the user 20 and from information from the device 10 or device 12, and, in one embodiment, the key is used to encode sensing data from the device 10 or 12 and the encoded data is transmitted to the remote server 18. There is performed a biometric measurement of the user 20 (such as a fingerprint) and the key is generated from this biometric measurement. Whichever device 10 or 12 is actually taking the measurement is used in combination with data from the user 20 to create the key to secure the data in such a way that the user 20 and device 10 or 12 can be securely identified.

A user ID extracted from their biometric measurement and a device ID from the respective device 10 or 12 can be combined at the application hosting device, component 14 in FIG. 1. Most of the measurement devices (PAN devices 10 and LAN devices 12 will not have fingerprint sensors on them due to their limited capabilities and the fingerprint sensors can be attached to the application hosting device 14. When the user takes the measurement, a device ID is also send to the hosting device 14 along with the measurement, where the biometric ID and device ID are combined to generate the key which is then used to sign (or authenticate) the data taken from the device 10 or 12.

Biometrics identify/authenticate people on what they are rather than on what they have (tokens) or what they know (passwords). Since biometric properties cannot be lost or forgotten, in contrast to tokens and passwords, they offer an attractive and convenient alternative to identify and authenticate people. However, private biometrics are usually not of a uniformly random nature and cannot be reproduced precisely each time a measurement is taken. To assist in this problem, "fuzzy extractors" are used to extract nearly uniform and reliable keys from the private biometrics.

Biometric information such as person's fingerprint or iris scan is clearly not a uniform random string, nor does it get reproduced precisely each time a measurement is taken. Due to this reason, fuzzy extractors are used to derive a nearly uniform randomness R from the biometric input. The extraction is also error tolerant in the sense that R will be the same even if the input changes, as long as it remains reasonably close to the original. Thus, a fuzzy extractor or helper data algorithm is required to extract one (or more) secure keys from noisy biometric data. For more information on these topics, see J. P. M. G. Linnartz and P. Tuyls, "New Shielding Functions to Enhance Privacy and Prevent Misuse of Biometric Templates" in Audio-and Video-Based Biometrie Person Authentication, AVBPA 2003, ser. LNCS, J. Kittler and M. S. Nixon, Eds., vol. 2688. Springer, June 9-11,2003, pp. 393-402. and Y. Dodis, M. Reyzin, and A. Smith, "Fuzzy extractors: How to generate strong keys from biometrics and other noisy data" in Advances in Cryptology, EUROCRYPT 2004, ser. LNCS, C. Cachin and J. Camenisch, Eds., vol. 3027. Springer-Verlag, 2004, pp. 523-540.

A fuzzy extractor requires two basic primitives, firstly information reconciliation or error correction and secondly privacy amplification or randomness extraction, which guarantees an output which is very close to being a uniformly distributed random variable. In order to implement those two primitives, helper data W are generated during the enrolment or registration phase. Later during the key reconstruction or authentication phase, the key is reconstructed based on a noisy measurement $R_i$ and the helper data W.

During the enrollment phase (carried out in a trusted environment), a probabilistic procedure called Gen is run. It takes as input a noisy biometric measurement R and produces as output a key K and helper data W: (K, W)←Gen(R). In order to generate the helper data W, an error correcting code C is chosen such that at least t errors can be corrected. The number of errors to be corrected depends on the particular application and on the quality of the biometric measurement. Once an appropriate code has been chosen, the helper data W is generated by first choosing a random code word $C_s$ from C and computing W1=$C_s$+R. Furthermore a universal hash function $h_i$ is chosen at random from a set H and the key K is defined as K←$h_i$(R). The helper data is then defined as W=(W1, i).

During the key reconstruction phase a procedure called Rep is run. It takes as input a noisy response R' and helper data W and reconstructs the key K (if R' originates from the same source as R) i.e. K←Rep(R',W). Reconstruction of the key is achieved by computing $C_s$'=W1+R', decoding $C_s$' to $C_s$ via the decoding algorithm of C, recovering R =$C_s$+W1, and finally computing K=$h_i$(R). The present method will work also with other types of helper data. For example, instead of XORing, it is also possible to perform a permutation.

As previously mentioned, the problem that is solved in the system is the authentication of the patient 20 and the device 10 or 12 which made the measurement. This is achieved by linking a measurement to both a device ID and the particular user. Each healthcare device 10 and 12 that is Continua certified has a unique Global ID. There are provided two main methods for combined user and device authentication. Firstly, a biometric measurement is directly mapped to a random error correcting code C and helper data is generated. However instead of directly mapping the biometric measurement, the biometric measurement and the global unique ID of the device 10 or 12 are mapped together to a random error correcting codeword.

In the second method, the Global Unique ID of the device, in combination with a random string, is mapped to a random codeword. Then during the registration of the user, this codeword is used during the generation of the biometric helper data. Hence the helper data of the biometric measurement is made dependent on the device Global Unique ID. As the secret codeword is now dependent on the device unique ID, it is possible to authenticate both device and the user at once. In all embodiments, described in the following, a string identifying the user will be used (usually written as Ui for some integer i). This string can be the name of the user, an email address, or some function of these "natural" identifiers (such as the least b significant bits of such identifiers).

It is assumed that the following are available on the device 10 or 12 that is being used, a ReadID algorithm which upon calling returns the Global Unique ID of the device (this is written as DIDi←ReadID (i); this notation means that the ReadID command is executed on device i), a GenBio algorithm which upon getting a biometric measurement BMu from user U outputs (Ku, Wu) (this is written as (Ku, Wu)←GenBio(BMu)), and a RepBio algorithm which upon getting a biometric measurement BMu' from user U and helper data Wu outputs the key Ku if BMu and BMu' are sufficiently close., (this is written as Ku←RepBio(BMu', Wu)).

In a first embodiment, the system would work as follows, in which A group of users U1, U2, U3, . . . , Un has a device i which measures some users' signal. The registration procedure of embodiment 1 is shown in the left hand side of FIG. 4. Step R1.1 means the first step in registration process of embodiment 1. In the right hand side of the Figure is shown the corresponding authentication process. Step A1.1 means the first step in authentication process of embodiment 1.

At step R1.1, if a user Uj is using device i for the first time then before running the GenBio algorithm, they run the algorithm ReadID as $D_{IDi}$←ReadID (i). Now after getting the $D_{ID}$, they obtain the biometric data Bmuj at step R1.2 and run the GenBio Algorithm on BMuj plus $D_{IDi}$ such as (Kuij, Wuij)←GenBio(BMuj∥$D_{IDi}$). Here "∥" could represent a simple concatenation or xoring of BMu and $D_{IDi}$. The output of the GenBio algorithm is almost uniform key Kuij and helper data Wuij which is dependent on both the biometric measurement—BMu and device global unique ID—$D_{IDi}$. This is step R1.3.

Steps R1.2 and R1.3 are repeated for every user who wants to use the device i. A database is stored in the device with entries as follows: (Uj ; Wuij), where Uj is a string identifying the user. It can be a name, an email address, a system generated identifier, a function of the previous ones (for example, the 16-bit least significant bits of a much longer identifier identifying the user),etc. Alternatively, the helper data could be indexed using Kuij. However, this is not desirable in terms of security as the key used to authenticate is stored in the clear. This is step R1.4.

The computed symmetric key "Kuij" is dependent on both the user's biometric and device global ID, and then transmitted in a secure manner to the health service provider, at step R1.5, together with the device ID and the identity of the user Uj. Note that due to privacy concerns Uj in different steps do not have to be the same identifiers, however in that case one-to-one mapping between them stored either at the device or at the server is required.

Figure 4:
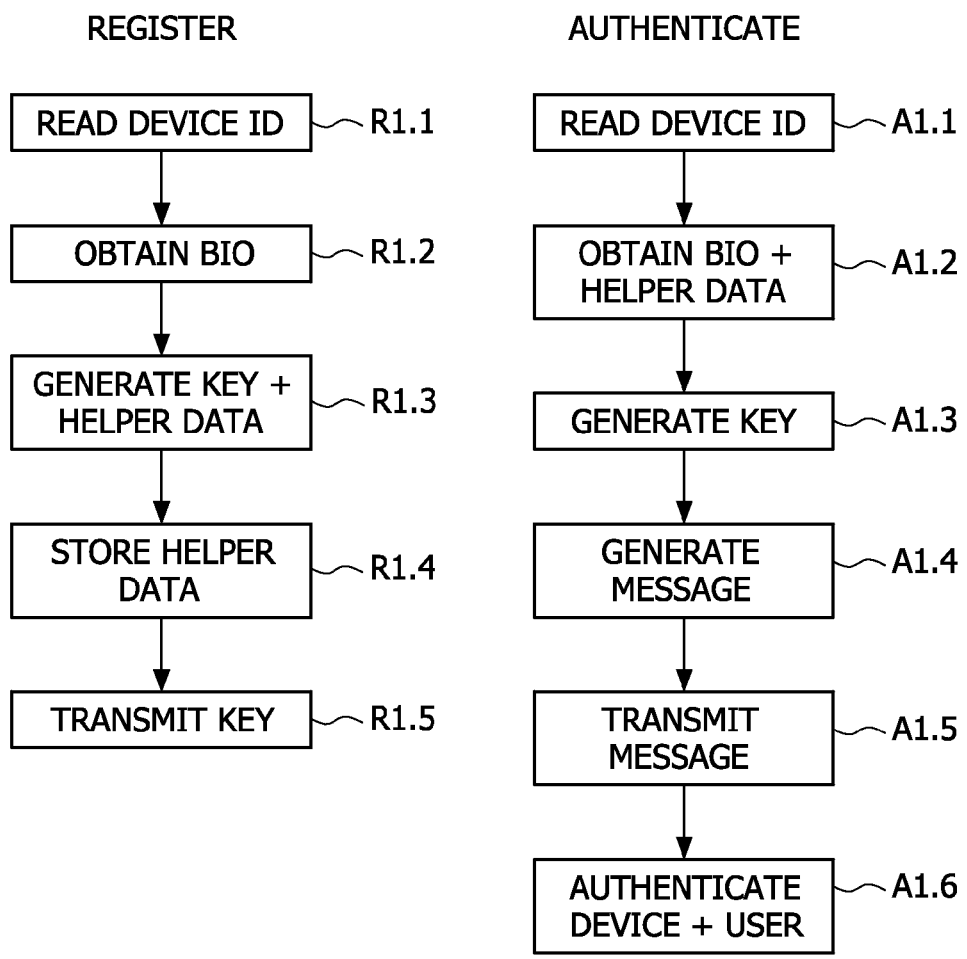
FIGS. 4 to 9 are flowcharts of respective registration and authentication procedures, and FIG. 10 comprising

The authentication procedure for embodiment 1 is also contained in FIG. 4. When a user Uj desires to use the device i to perform a measurement, before being able to operate the device, user Uj runs $D_{IDi}$←ReadID( ), shown in step A1.1. After getting $D_{IDi}$, Uj recalls the helper data and obtains there biometric data BMuj, step A1.2. They then run Kuij ←RepBio(BMuj'||$D_{IDi}$,Wuij) and recover Kuij, step A1.3.

The user's data is measured and a Message Authenticating Code (MAC) on the data is computed using Kuij, step A1.4. The MAC can be a dedicated MAC or a keyed hash function. The data and MAC are sent to the service provider, step A1.5, together with the identity of the user Uj (for example the user ID, the email address, etc.). Authentication of the user and the device are then carried out, step A1.6. The service provider searches its database for the identity of the user, and checks the MAC for all keys registered for this user. If the MAC verifies successfully for one of these keys, the data is accepted and assigned to the device whose key was used. Otherwise, the data is rejected and a notification sent back to the user (optional).

An alternative would be to send both user ID and device ID in step A1.5 together with the MAC. Then the service provider has to check a single MAC. This is at the cost of additional data bandwidth being used in Step A1.5. If there is a privacy concern related to sending the user identity information and device IDs over the channel, a number of existing pseudo-randomization and encryption techniques can be used to address these concerns. It is even possible to send in step A1.5 only the data and MAC and let the server find which device and user sent the data in A1.6.

Figure 5:
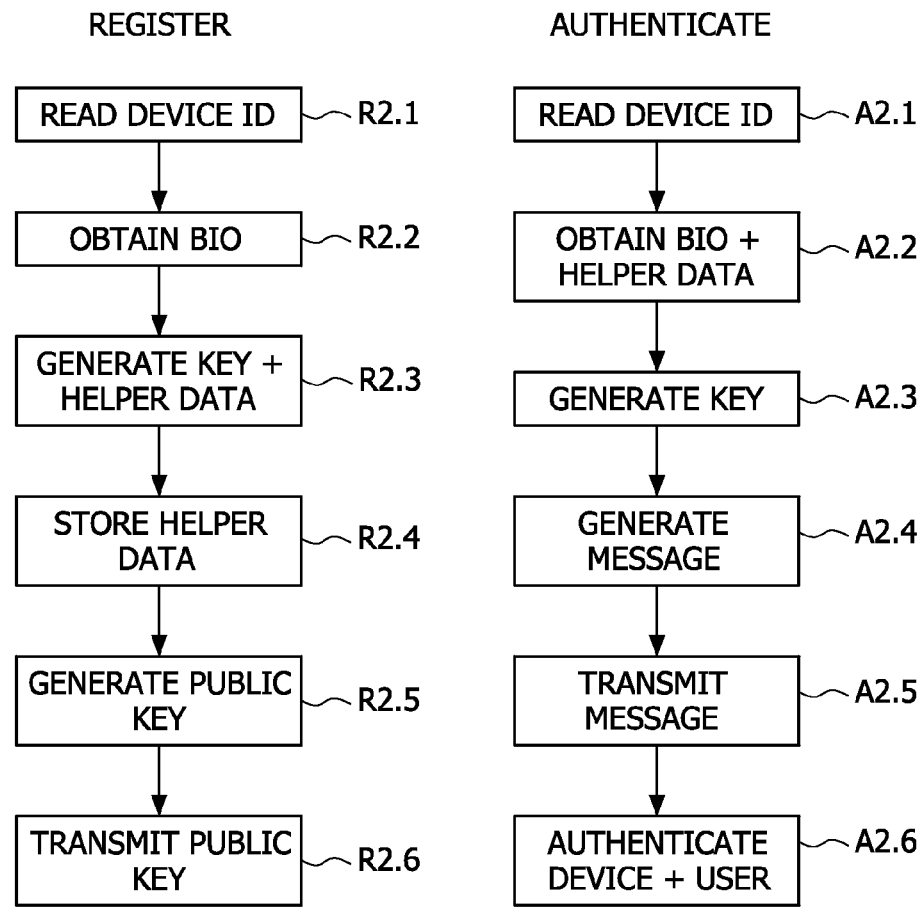

An alternative method using public-key cryptography, embodiment two, is shown in FIG. 5. The system would work on the same basis that a group of users U1, U2, U3, . . . , Un. have a device i which measures some signal of users. The registration procedure of embodiment two is shown in the left hand side of FIG. 5, and the authentication procedure is shown in the right hand side of FIG. 5.

If the user Uj is using device i for the first time, then before running the GenBio algorithm, they run the algorithm ReadID such that $D_{IDi}$←ReadID (i), step R2.1. This user's device performs a computation for the user after an initialization or a signal indicating that the computation needs to be performed. After getting the $D_{IDi}$, they obtain BMuj (step R2.2) and run GenBio Algorithm on BMuj plus $D_{IDi}$ such that (Kuij, Wuij)←GenBio(BMuj||$D_{IDi}$). Here "||" could represent a simple concatenation or xoring of BMu and $D_{IDi}$. The output of the GenBio algorithm is an almost uniform key Kuij and helper data-Wuij which is dependent on both the biometric measurement BMu and device global unique ID $D_{IDi}$. This is step R2.3. These two steps are repeated for every user who wants to use the device. A database is stored in the device with entries as follows: (Uj; Wuij), step R2.4.

The computed key Kuij is dependent on both the user's biometric and device global ID, and is used as the private key for the user j and device i pair. Depending on the public-key cryptosystem used, the user runs a public-key generation process which has as input the private key Kuij and outputs a public key Kuij_pub. This is the step R2.5.

Kuij_pub is then transmitted in a secure manner and authenticated manner to the health service provider, step R2.6, together with the device ID and the identity of the user. Alternatively, a certificate authority (or the service provider) can create a public-key certificate for the user and his devices in the enrolment phase (these certificates will contain the user identity information, the device identity information, the public key for that user/device pair Kuij_pub, and perhaps other personal data information such as age, address, etc. All this information would then be signed by the private key of the certificate authority. If self certification is used, then the user will sign this data with his private key Kuij.

In the authentication procedure for embodiment, user Uj desires to use device i to perform a measurement. Before being able to operate the device, user Uj runs $D_{IDi}$←ReadID( ), step A2.1. After getting $D_{IDi}$, Uj recalls the helper data and obtains there biometric data BMuj, step A2.2 and then runs Kuij←RepBio(BMuj'||$D_{IDi}$,Wuij) and recovers Kuij, step A2.3. The sensing data is measured and signed using Kuij, step A2.4.

The data and signature are sent to the service provider, together with the user/device certificate containing the public-key Kuij_pub. The user/device certificate can be sent only once and stored at the backend system. This is step A2.5. The service provider searches its database for the certificate of the user, and checks the signature. If the signature verifies successfully, the data is accepted and assigned to the user-device pair or simply to the user (since we are interested in storing user data as long as the data has been correctly generated) whose key was used. Otherwise, the data is rejected and a notification sent back to the user (optional). This is step A2.6.

In the current embodiment, an alternative method for the combined user and device authentication is possible. The main idea is to generate the helper data based on the Global Unique ID of the device-$D_{ID}$. It can be assumed that each device has a non-modifiable Global Unique ID (such as MAC address etc). This Global Unique ID concatenated with an additional new random string is mapped to a codeword C and helper data for the biometric is generated based on the codeword C. This alternative is shown in FIG. 6.

The proposed registration procedure would work on the basis of a group of users having a device i which measures some signal of the users U1, U2, U3, . . . , Un. At step R3.1 the device ID $D_{ID}$, is obtained. Prior to using the device for the first time, a user Uj runs a procedure encode on the device i ID and obtains Ci←Encode($D_{ID}$||γi), where "γi" is a random string, and Ci is a codeword. This is step R3.2. The random string "γi" should be different for each user. The purpose of γi is to make the helper data of the appropriate size for the biometric.

User Uj obtains their biometric data, step R3.3, and then runs the procedure GenHelperData( ) in order to generate the helper data. GenHelperData operates on the codeword "Ci" produced in the step R3.2 and the digitized biometric measurement, BMuj, to produce (Kuij,Wuj,i)←GenBio'(Ci, BMuj). Ci is used then as the randomness usually used in the generation of a pseudo-identity in biometric systems. This is step R3.4. This step is repeated for every user who wants to use the device. A database is stored in the device with entries as follows: (Uj; Wuj,i), step R3.5. The value of Kuij is sent to the server in a secure and authenticated manner together with the device ID $D_{ID}$, and the user name Uj, step R3.6.

Figure 6:
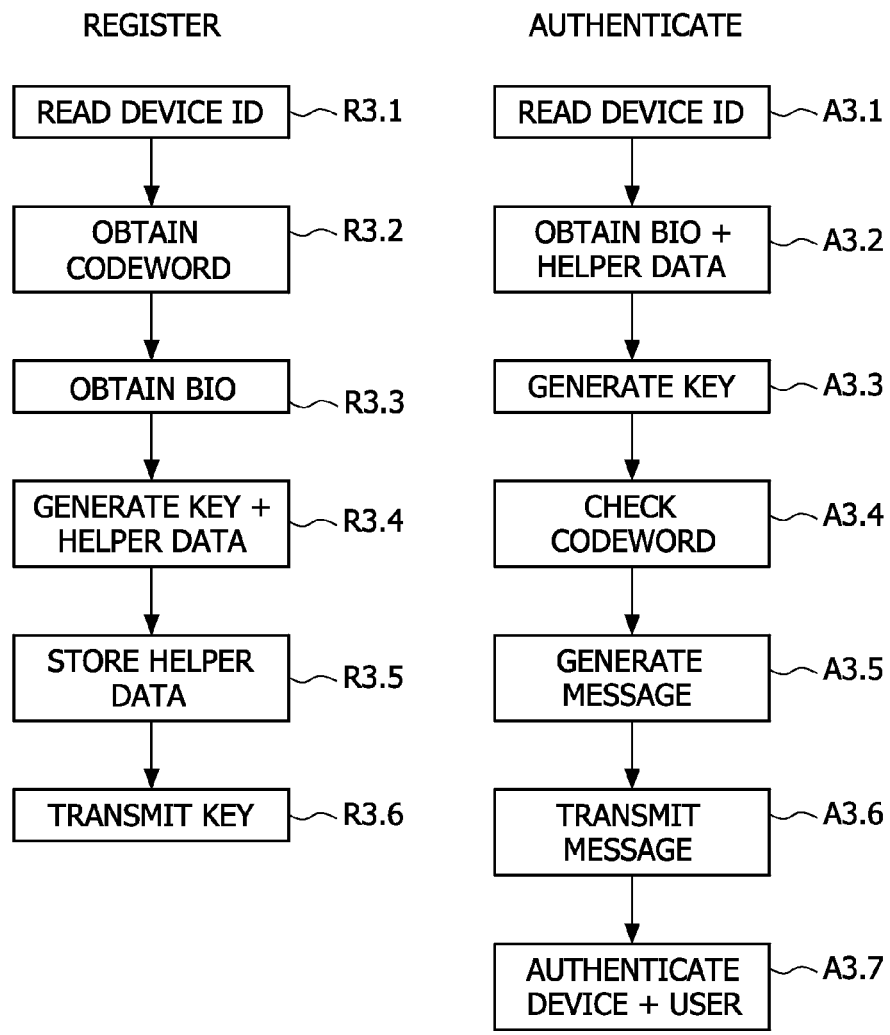

The authentication procedure for this methodology is also shown in FIG. 6. User Uj desires to use device_i to perform a measurement. User Uj reads the device ID as $D_{IDi}$←ReadID( ), which is step A3.1. The user Uj makes a biometric measurement and recovers the helper data corresponding to the device ID $D_{IDi}$, from the local database, step A3.2, and runs Kuij←RepBio(BMuj',Wuj,i) and recovers Kuij, step A3.3. During the procedure RepBio, the codeword Ci has to be reconstructed. Thus, it is possible to check if the first part of the code word Ci corresponds to $D_{IDi}$, step A3.4. If it does not, the authentication procedure could be aborted or a warning sent to the user.

Device_i computes a Message Authentication Code (MAC) on the data measured with secret key Kuij, step A3.5 and sends the data and the MAC to the health service provider together with the user ID and (possibly) the device ID, step A3.6. The health service provider verifies the MAC by retrieving the key corresponding to the user and device ID and if the verification succeeds the data is accepted, step A3.7. This same registration and authentication procedures can be easily modified as was embodiment one, to accommodate public-key primitives (signatures) instead of MACs.

Figure 7:
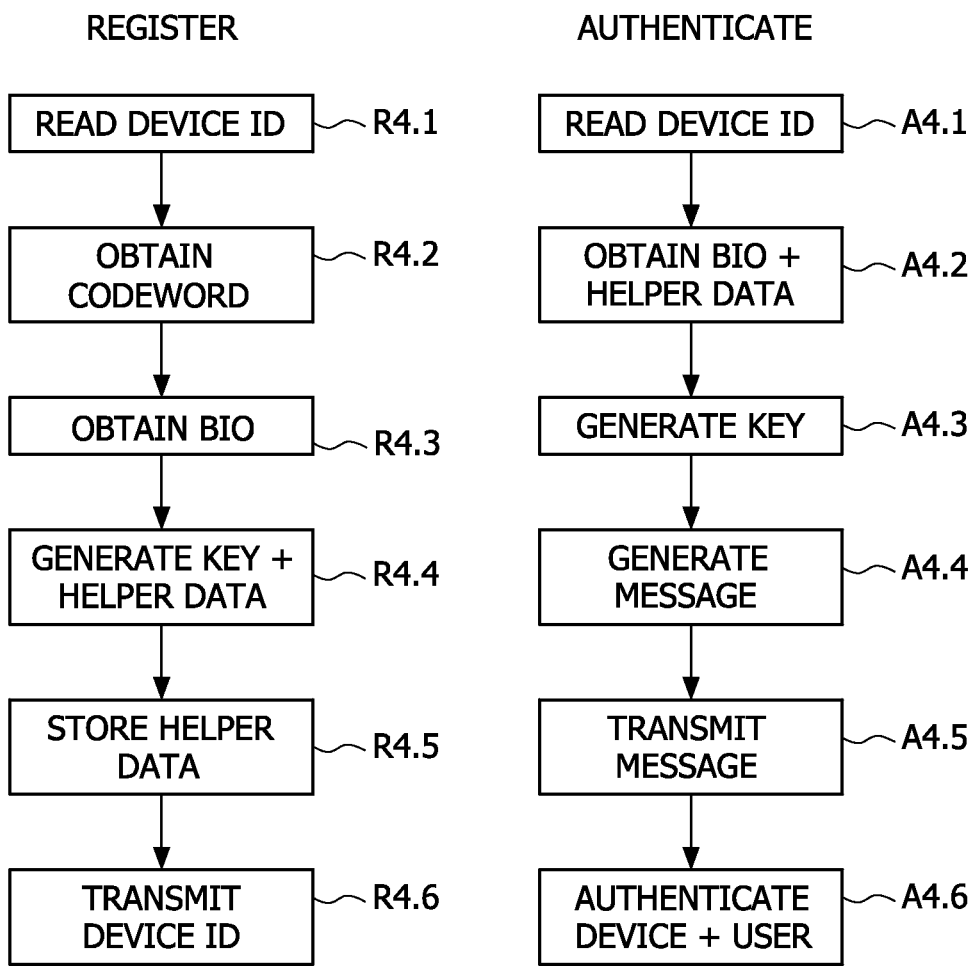

A more secure variation is possible. The above procedure allows someone to obtain partial information about the biometrics of the user if the device ID $D_{IDi}$ becomes known. To avoid this, it is possible to perform the following variation, as shown in FIG. 7.

In the registration procedure, as before, a group of users has a device i which measures some signal of users U1, U2, U3, . . . , Un. At step R4.1 the device ID $D_{IDi}$, is obtained. Prior to using the device for the first time, a user Uj runs the procedure encode on a function of the device i ID (this function could be a hash function but also a subset of the bits representing the ID, for example) and a nonce and obtains Ci←Encode(f($D_{IDi}$∥γi)), where "γi" is a random string, and Ci is a codeword. The random string "γi" should be different for each user. The purpose of γi is twofold: (i) making the helper data of the appropriate size for the biometric and (ii) making Ci unpredictable from knowledge of the device ID. The random nonce γi should be kept secret. The function f can be any function of its arguments. Preferably, it should be a cryptographically secure one-way function such as a hash function (SHA-1, SHA-2, etc.). This is step R4.2.

The user Uj obtains their biometric data, step R4.3, and runs the procedure GenHelperData( ), in order to generate the helper data. GenHelperData operates on the codeword "Ci" produced in the step 1 and the digitized biometric measurement, BMuj, as follows: (Kuij,Wuj,i)←GenBio'(Ci, BMuj). Ci is used then as the randomness usually used in the generation of a pseudo-identity in biometric systems. This is step R4.3. This step is repeated for every user who wants to use the device. A database is stored in the device with entries as follows: (Uj; Wuj,i), step R4.5.

The following values are then sent to the remote service: ($D_{IDi}$, γi, Uj) in a secure and authenticated manner, as step R4.6. It is also possible to send Kuij to the server, although not necessary. In some situations, sending Kuij might result in a performance advantage for the server, since then the server does not have to compute a new the key every time data is received. In addition, doing this prevents the user's biometric measurement from being leaked. On the other hand, sending the triplet ($D_{IDi}$, γi, Uj) results in a security advantage for two reasons, firstly if an attacker compromises temporarily the server the key Kuij is not compromised and secondly the key is computed again for every new set of data, this results in a system more tolerant to errors. However, this variant has the disadvantage that the biometric of the user is leaked, i.e. this method is not privacy preserving.

The corresponding authentication procedure for FIG. 7 works as follows. User Uj desires to use device i to perform a measurement. User Uj reads the device ID as D $D_{IDi}$←ReadID( ), step A4.1. The user Uj makes a biometric measurement and recovers the helper data corresponding to his user ID Uj from the local database, step A4.2, and runs Kuij ←RepBio(BMuj',Wuj,i) and recovers Kuij, step A4.3.

The device i computes a Message Authentication Code (MAC) on the measured data with secret key Kuij, step A4.4, and sends the data and the MAC to the health service provider together with the user ID and associated helper data Wuj,i, step A4.5. The health service provider verifies the MAC by re-computing the key Kuij from ($D_{IDi}$, γi, Uj) and the helper data Wuj,i, corresponding to the user and device ID, verifies the MAC, and if the verification succeeds the data is accepted. This is step A4.6. The service provider knows the ID of the device by searching for the ID that corresponds to the helper data Wuj,i sent by the user in the authentication procedure. If the key Kuij had been stored already in the database of the server (as suggested in of the enrolment procedure 4, then it is not necessary to re-compute Kuij).

It is possible that in certain situations the user will want to keep the ID of the device used to make medical measurements secret and only known to the service provider. In these cases, the following embodiment is of use. The basic idea in this embodiment is to use the key derived from the biometric to compute a function of the device ID. The right value for the function can only be computed by the user whose biometric is being used. There is computed a function of the device ID using the biometric derived secret as a key.

Figure 8:
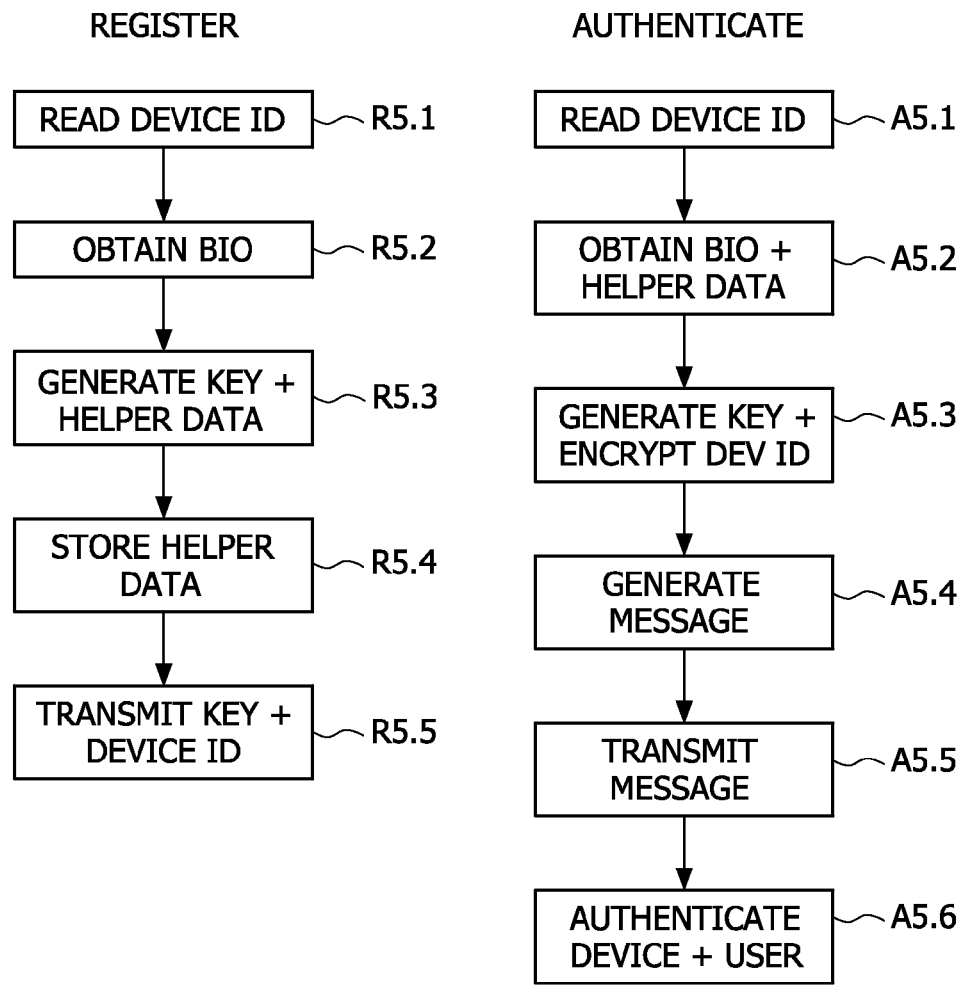

In this procedure the enrolment and authentication are shown in FIG. 8. A group of users U1, U2, U3, . . . , Un have a device i which measures some signal of the users. At step R5.1, the device ID $D_{IDi}$ is read. The user Uj measures their biometric, step R5.2, and produces helper data and a key as (Kuj,Wuj)←GenBio(BMuj), step R5.3. The helper data Wuj is stored wherever the biometric reconstruction will take place, for example in the home hub which collects all the measurements from the devices and sends them to the server. This is step R5.4.

User Uj sends Kuj and $D_{IDi}$ corresponding to the ID of device i to the server, at step R5.5. Step R5.3 is repeated for every user who wants to use the device. Per user the following information is sent to the server: (Kuj; $D_{IDi}$,Uj). A database is stored in the server with entries as follows: (Kuj; $D_{IDi}$, Uj), where Uj is the identity of the user.

The corresponding authentication procedure is shown in the right hand side of FIG. 8. User Uj desires to use device i to perform a measurement. At step A5.1 the device ID $D_{IDi}$ is read. The user then makes a biometric measurement and also obtains the stored helper data, at step A5.2. Before being able to operate the device, user Uj runs Kuj←RepBio(BMuj,Wuj) and recovers Kuj. The device ID, $D_{IDi}$ is encrypted using Kuj to produce yi←EncKuj($D_{IDi}$) or any function of $D_{IDi}$ and Kuj in general that cannot be inverted without knowledge of Kuj. This is step A5.3. The non-invertibility criterion is important since in most cases $D_{IDi}$ is a public value. To make it less susceptible to replay attacks it is possible to compute yi←f (Kuj, $D_{IDi}$, γi), where γi is a nonce or a counter for some appropriate function f. The function f can be a signature, a hash function, or an encryption function, for example.

The device i then computes a Message Authentication Code (MAC) on the data measured and the encrypted yi with secret key Kuj, step A5.4 and sends the data, yi and the MAC to the health service provider together with the string identifying the user Uj. This is step A5.5. An equivalent public-key method can be used. The health service provider verifies the MAC, decrypts the yi with help of its knowledge of Kuj and verifies that the result corresponds to a device $D_{IDi}$ in its database and if the verification succeeds the data is accepted, at step A5.6.

Figure 9:
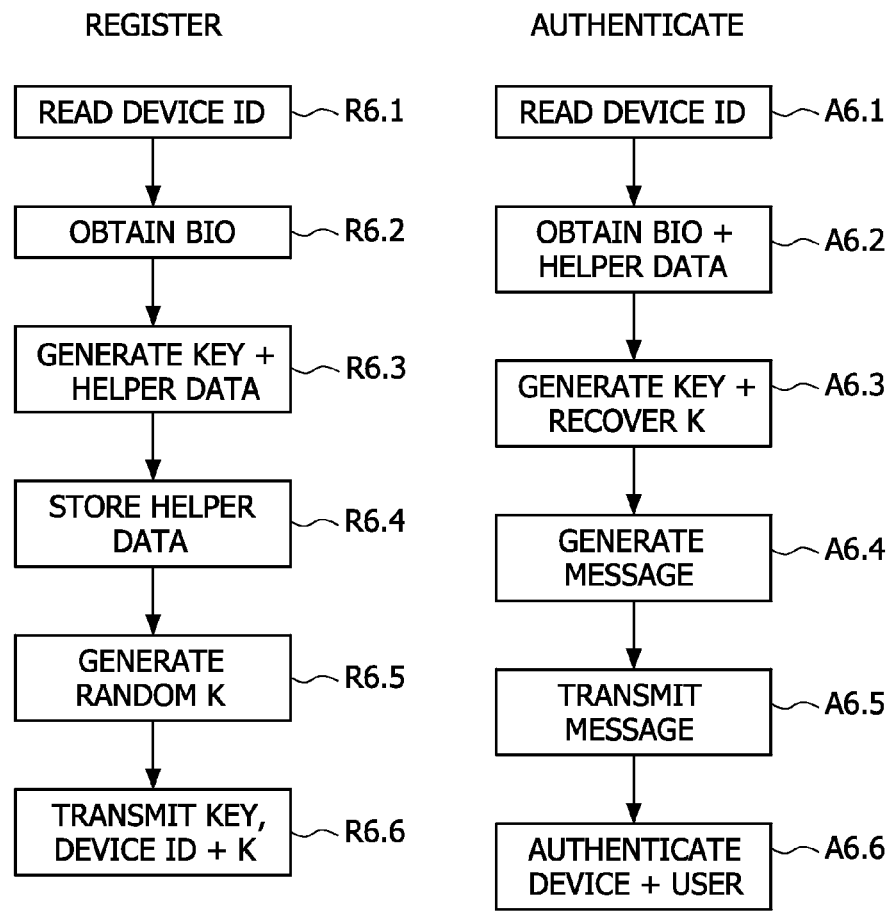

A less efficient variation is also possible. It is also possible to operate the device and user authentication using a computed device helper data. This is described below with reference to FIG. 9. The registration process, left hand side of the FIG. 9, is described first. The group of users U1, U2, U3, . . . , Un have a device i which measures some signal of the users. The device ID is read first, step R6.1. The user Uj measures his biometric, step R6.2, and produces helper data and a key as (Kuj,Wuj)←GenBio(BMuj), step R6.3. The helper data Wuj is stored, at step R6.4, wherever the biometric reconstruction will take place, for example in the home hub which collects all the measurements from the devices and sends them to the server.

The next step in the registration is step R6.5 in which a secret and random value Ki is generated. Additional helper data Wi,uj is generated as follows Wi,uj=Ki+Kuj, where "+" denotes the XORing of Ki and Kuj. The data Wi,uj is stored in the device making the measurement or in the hub. These steps are repeated for every user who wants to use the device. And per user the following information is sent to the server: (f(Kuj, Ki, $D_{IDi}$);$D_{IDi}$, Uj), in step R6.6. Here f is some function of Kuj and Ki (and possibly a random nonce or non-repeating counter) as in previous embodiments. A database is stored in the server with entries as follows: (f(Kuj,Ki,$D_{IDi}$); $D_{IDi}$, Uj), where Uj is the identity of the user.

The corresponding authentication procedure works as follows. The user Uj desires to use the device i to perform a measurement, and obtains the device ID at step A6.1. Before being able to operate the device, the user Uj obtains their biometric data, step A6.2, and runs Kuj←RepBio(BMuj, Wuj) and recovers Kuj. The value Ki is recovered by computing Ki=Wi,uj+Kuj, which is step A6.3. A key Kuj,i is derived as Kuj,i←f(Kuj,Ki, $D_{IDi}$). There is then performed the operations as in previous embodiments (MAC computation on data, sending data and MAC to the server, and verification on the server side of the appropriate values), as detailed in steps A6.4 to A6.6.

All of the protocols have been described in terms of computing MACs or signature. Similarly, it is possible to compute an encryption and then a MAC over the encryption of the data being sent to the service provider. If this is done, then there would need to be two keys derived. This can be easily accomplished by using additional randomness and performing additional registration procedures for the biometric (i.e. deriving a second key from the biometric measurement). A single key per user and for a family of devices can be computed using secret sharing schemes.

There are several advantages to the various embodiments of the invention. Most importantly, the approach allows authentication from which device and user the data is originating. In establishing data provenance the system couples very early the device and user identifiers that can be obtained by strong authentication mechanisms, using a Unique Global Device ID and biometrics. In this approach, the key derivation is performed in one step which leads to higher reliability. Furthermore, the approach is advantageous because there is a need to register with the service provider a key per user device pair. This supports separation of duties. The service provider or EHR infrastructures does not have to take care of registration of measurement devices. Finally, depending on the embodiment chosen for implementation, it is possible to identify a user who has not been registered before, which also contributes to the reliability of the measured data.

Figure 10A:
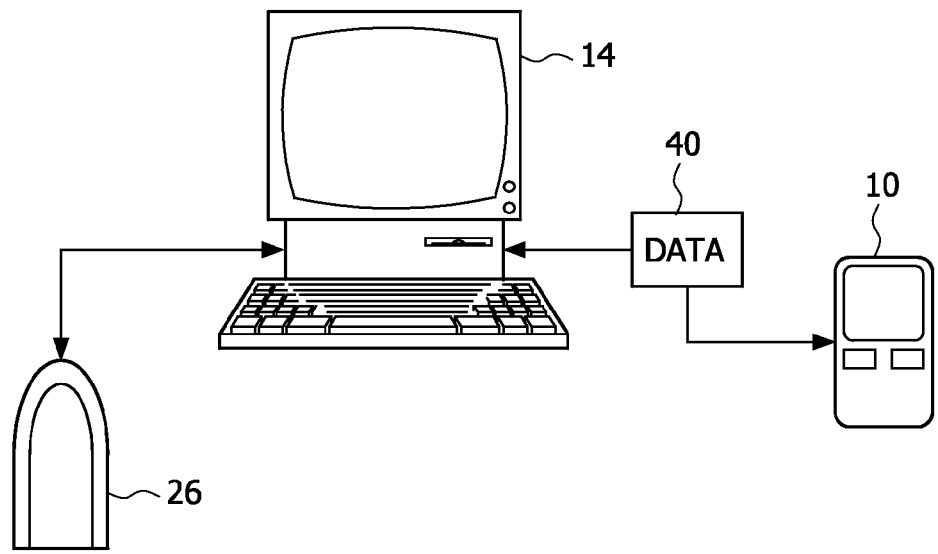
FIGS. 10a and 10b is a schematic diagram of a preferred embodiment of the authentication system.

A preferred embodiment of the invention is shown in FIG. 10. In this Figure, the application hosting device 14, the home hub, is connected to a sensing device 10 and also to a biometric measuring apparatus 26. The device 10 is a device for measuring sensing data 40 (in this example the blood pressure) of the user 20, and the biometric measuring apparatus 26 is a device for measuring the fingerprint of the user 20, when the user 20 places their finger into the device 26. The system of this Figure assumes that the registration process has already taken place and the user 20 has performed the measurement of their blood pressure with the device 10. The user 20 wishes to authenticate the acquired sensing data 40 prior to sending that acquired data 40 to a third party health service provider.

Figure 10B:
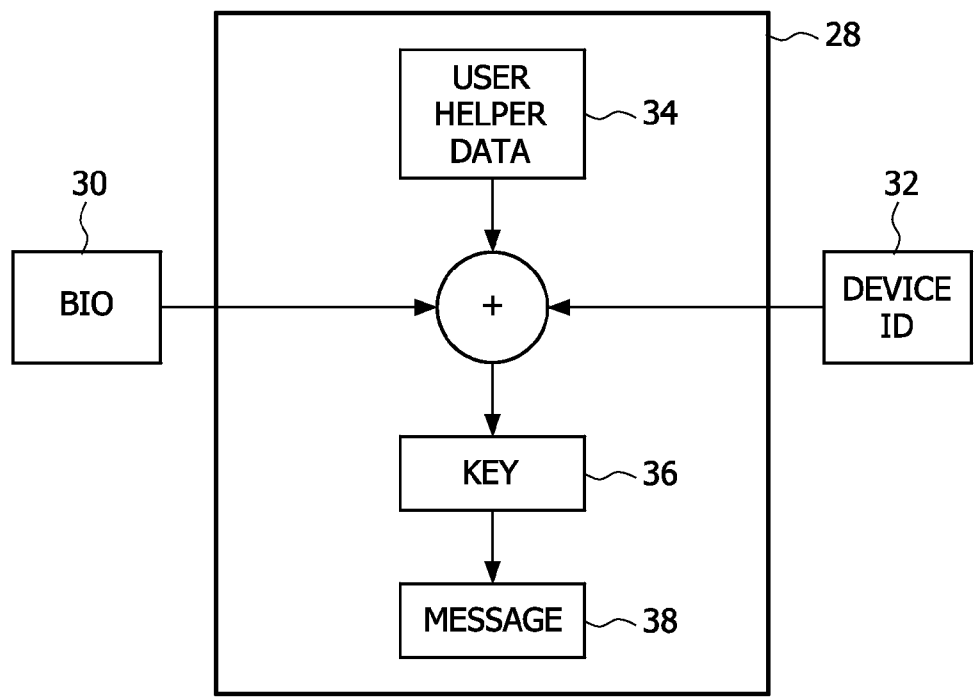

FIG. 10b illustrates the actions taken by a processor 28, which forms part of the hosting device 14. The biometric measurement 30 of the user's fingerprint is received by the processor 28, from the biometric measuring apparatus 26. The device ID 32 is also received from a query applied to the device 10. Within the system is present a query component which makes a query to the device 10. This component (not shown) could be built in within the device 10. The biometric measurement 30 is combined with user helper data 34, and in this preferred embodiment, also combined with the device ID 32, to generate a key 36, and the key 36 is then used to compose a message 38 which includes the sensing data 40, which is then transmitted to the remote service. Authentication of the user 20 and device 10 is then carried out, and the data 40 contained within the message 38 can be relied on, as the user 20 and the device 10 have been securely identified.

The invention claimed is:

1. A personal healthcare method comprising:
registering a physiological data measuring device which has a unique device ID and is configured to make a physiological data measurement, including:
performing a biometric measurement of a user,
extracting a key and helper data for the user from the biometric measurement, the helper data being configured to extract the key from the biometric data,
storing the helper data in the physiological data measuring device,
electronically transmitting the device ID and an ID of the user to a remote server which includes a remote server computer processor and is associated with an electronic data storage configured to store physiological data measurements of a plurality of users;
authenticating the device and the user including with a physiological data site computer processor:
receiving a current biometric measurement and a current physiological data measurement of the user,
retrieving the helper data for the user,
generating the key from the current biometric measurement and the helper data,
generating a message including the current measured physiological data and one of (a) a message authenticating code derived from the current measured physiological data and the key or (b) a signature for the current measured physiological data derived from the key,
electronically transmitting the message to the remote server, and
with the remote server computer processor of the remote server, authenticating the device and the user with the message and the device ID and the user ID which was transmitted during the registering step.

2. The method according to claim 1, wherein
the step of generating the current key includes generating the current key and the helper data for the user from the current biometric measurement and the device ID;
the step of storing the helper data includes storing the helper data in the physiological data measuring device along with the user ID;
the step of transmitting the device ID and the user ID to the remote server further includes transmitting the key to the remote server; and
the step of authenticating the physiological data measuring device and the user in the remote server includes authenticating the physiological data measurement device and the user with the message and the device ID, the user ID, and the key transmitted during the step of registering.

3. The method according to claim 2, wherein the step of generating the key and the helper data for the user from the biometric measurement and the physiological data measurement device ID includes generating a codeword from the physiological data measurement device ID and a random string, and generating the key from the codeword and the biometric measurement.

4. The method according to claim 2, and further including in the message the physiological data measurement device ID and/or the user ID.

5. The method according to claim 1, wherein
registering the physiological data measurement device and the user in the system server further includes the step of generating a codeword from the device ID and a random string;
the step of generating the key and the helper data for the user from the biometric measurement includes generating the key and the helper data for the user from the biometric measurement and the codeword;
the step of storing the helper data includes storing the helper data in the physiological data measurement device along with the user ID;
the step of transmitting the device ID and the user ID to the remote server further includes transmitting the random string to the remote server ; and
the step of authenticating the physiological data measurement device and the user in the remote server includes authenticating the physiological data measurement device and the user with the message and the device ID, the user ID, and the random string transmitted during the step of registering.

6. The method according to claim 1, wherein
the step of transmitting the device ID and the user ID to the remote server further includes transmitting the key to the remote server;
authenticating the device and the user with the remote server further includes encrypting the device ID using the key;
the generated message further includes the encrypted device ID; and
the step of authenticating the physiological data measurement device and the user in the remote server includes authenticating the physiological data measurement device and the user with the message and the device ID, the user ID, and the key transmitted during the step of registering.

7. The method according to claim 1, wherein
registering the physiological data measurement device and the user in the system further includes generating a random value and generating an additional helper data from the random value and the key;
the step of storing the helper data further includes storing the additional helper data;
the step of transmitting the device ID and the user ID to the remote server further includes transmitting a function of the key, a random value, and the device ID to the remote server;
retrieving the helper data further includes retrieving the additional helper data;
authenticating the physiological data measurement device and the user with the remote server further includes obtaining the random value from the additional helper data and the key and generating an additional key from the function of the key, the random value, and the device ID;
the message generating step includes deriving the message authenticating code from the measured physiological data and the additional key; and
the step of authenticating the physiological data measurement device and the user in the remote server includes authenticating the physiological data measurement device and the user with the message, the device ID, the user ID, the function of the key, the random value, and the device ID transmitted during the step of registering.

8. A system for authenticating a device and a user comprising:
a measurement apparatus configured to perform a biometric measurement of the user;
a sensing device configured to measure physiological data of the user, the sensing device including an electronic memory having a device ID stored therein;
a remote server;
a processor apparatus configured to:
during a procedure for registering the sensing device and a user with a remote server:
retrieve the device ID for the sensing device from the sensing device electronic memory,
receive a biometric measurement of the user from the measurement apparatus,
generate a key and helper data for the user from the biometric measurement, the helper data being configured for extracting one or more keys from biometric measurements,
store the helper data in a processor electronic memory,
electronically transmit the device ID and a user ID to the remote server, and
during a procedure for authenticating the sensing device and the user with the remote server:
receiving a current biometric measurement and currently measured physiological data,
obtain the device ID for the sensing device from the sensing device,
retrieve the helper data for the user,
generate a key from the current biometric measurement and retrieved helper data,
generate a message including the current measured data and either (a) a message authenticating code derived from the currently measured data and the key or (b) a signature for the measured data derived from the key, and
transmit the message to the remote service,
wherein the remote server is configured to authenticate the sensing device and the user with the message and the device ID and the user ID received during the registration procedure.

9. The system according to claim 8, wherein the processor apparatus is further configured to:

generate the key and the helper data for the user from the biometric measurement and the device ID;

store the helper data in the sensing device along with the user identity;

transmit the key to the remote server along with the device ID and the user ID; and wherein the remote server is further configured to authenticate the sensing device and the user with the message and the device ID, the user ID, and the key transmitted during the procedure for registering.

10. The system according to claim 9, wherein the processor apparatus is further configured to generate the key and the helper data for the user from the biometric measurement and the device ID by generating a codeword from the device ID and a random string, and generating the key from the codeword and the biometric measurement.

11. The system according to claim 9, wherein the processor apparatus is further configured to include in the message the device ID and/or the user ID.

12. The system according to claim 8, wherein during the registering of the sensing device and the user, the processor apparatus is further configured to:

generate a codeword from the device ID and a random string, generate the key and the helper data for the user from the biometric measurement and the codeword, store the helper data in the sensing device along with a user identity, transmit the random string to the remote service along with the device ID and the user ID; and wherein the remote server is configured to authenticate the sensing device and the user with the message and the device ID, the user ID, and the random string transmitted during the registering.

13. The system according to claim 8, wherein the processor apparatus is further configured to:

transmit the key to the remote server along with the device ID and the user ID, encrypt the device ID using the key during the authenticating of the sensing device and the user with the remote server, generate the message including the encrypted device ID; and wherein the remote server is configured to authenticate the sensing device and the user with the message and the device ID, the user ID, and the key transmitted during the registering.

14. The system according to claim 8, wherein the processor apparatus is further configured to:

generate a random value and additional helper data from the random value and the key during the registration of the sensing device and the user, store the additional helper data, transmit a function of the key, the random value, and the device ID to the remote server along with the device ID and the user ID, retrieve the additional helper data, obtain the random value from the additional helper data and the key and generate an additional key from the function of the key, the random value, and the device ID during the authentication of the sensing device and the user with the remote server, generate the message authenticating code from the measured data and the additional key; and wherein the remote server is configured to authenticate the sensing device and the user with the message and the device ID, the user ID, and the function of the key, the random value and the device ID transmitted during registering.

15. A personal health record system comprising:

a sensing device configured to sense physiological data of a user, the sensing device having a sensing device ID;

a measurement device configured to perform a biometric measurement on the user to generate biometric data;

a hub device including a hub computer processor and a transmitter configured to transmit encoded physiological data over a data channel, the hub computer processor being connected with the sensing device to receive the physiological data and the sensing device ID, and with the measurement device to receive the biometric data;

a remote server configured to receive the encoded physiological data from the data channel, authenticate the encoded physiological data and store the authenticated physiological data of the user in a personal health record of the user corresponding to the user in a health record system of a third party healthcare provider, the remote server including a server computer processor;

the hub and server computer processors being configured to register the sensing device and the user, wherein the hub computer processor is configured to:

generate from the biometric data helper data with which keys are extractable from the biometric data, store the helper data in a hub memory, cause the transmitter to transmit the helper data, the device ID, and a user ID to the sensor computer processor; and the hub and server computer processors are further configured to authenticate the physiological data, wherein the hub computer processor is further configured to:

generate a key from the helper data and the biometric data, generate a message including current physiological data and one of (a) the key and a message authenticating code derived from the physiological data and (b) a signature for the current measured data derived from the key, control the transmitter to transmit the message; and wherein the server computer processor is further configured to:

authenticate the sensing device and the user with the message and the device ID and the user ID receive during registration.

16. The system according to claim 15, wherein the hub computer processor is further configured to:

generate the key and the helper data for the user from the biometric measurement and the device ID;

store the helper data along with the user ID;

transmit the key to the server computer processor along with the device ID and the user ID; and wherein the server computer processor is further configured to authenticate the sensing device and the user with the message and the device ID, the user ID, and the key transmitted during registration.

17. The system according to claim 16, wherein the hub computer processor is further configured to generate the key and the helper data for the user from the biometric measurement and the device ID by generating a codeword from the device ID and a random string, and generating the key from the codeword and the biometric measurement.

18. The system according to claim 15, wherein
during the registering of the sensing device and the user, the
  hub computer processor is further configured to:
    generate a codeword from the device ID and a random string,
    generate the key and the helper data for the user from the biometric measurement and the codeword,
    store the helper data in the sensing device along with the user ID,
    transmit the random string to the server computer processor along with the device ID and user ID; and
  wherein the server computer processor is configured to authenticate the sensing device and the user with the message and the device ID, the user identity, and the random string transmitted during registration.

19. The system according to claim 15, wherein
the hub computer processor is further configured to:
    transmit the key to the server computer processor along with the device ID and the user ID,
    encrypt the device ID using the key during the authentication of the sensing device and the user with the computer processor,
    generate the message including the encrypted device ID; and
  wherein the server computer processor is configured to authenticate the sensing device and the user with the message and the device ID, the user ID, and the key transmitted during registration.

20. The system according to claim 15, wherein
the hub computer processor is further configured to:
    generate a random value and additional helper data from the random value and the key during the registration of the sensing device and the user,
    store the additional helper data,
    transmit a function of the key, the random value, and the device ID to the server computer processor along with the device ID and the user ID,
    retrieve the additional helper data,
    obtain the random value from the additional helper data and the key and generate an additional key from the function of the key, the random value, and the device ID during the authentication of the sensing device and the user with the server computer processor,
    generate the message authenticating code from the measured data and the additional key; and
  wherein the server computer processor is configured to authenticate the sensing device and the user with the message and the device ID, the user ID, and the function of the key, the random value and the device ID transmitted during registration.

* * * * *